United States Patent [19]

Korczak

[11] 4,389,886
[45] Jun. 28, 1983

[54] CALIBRATING UNIT
[75] Inventor: Roman L. Korczak, Des Plaines, Ill.
[73] Assignee: Lutheran General Hospital, Inc., Park Ridge, Ill.
[21] Appl. No.: 239,338
[22] Filed: Mar. 2, 1981
[51] Int. Cl.³ .................................... G01M 19/00
[52] U.S. Cl. .................................... 73/168; 73/1 R; 73/3
[58] Field of Search ............... 73/1 R, 3, 861.41, 168; 128/214 E

[56] References Cited

U.S. PATENT DOCUMENTS

| | | |
|---|---|---|
| 2,664,907 | 1/1954 | Lowe . |
| 2,830,191 | 4/1958 | McCollom et al. . |
| 3,079,795 | 3/1963 | Kowallis ............... 73/861.77 |
| 3,517,308 | 6/1970 | Mirdadian . |
| 3,593,579 | 7/1971 | Hindman ............... 73/861.41 |
| 3,736,930 | 6/1973 | Georgi . |
| 3,754,220 | 8/1973 | Sztamler et al. . |
| 3,770,239 | 11/1973 | Stobbe et al. . |
| 3,800,794 | 4/1974 | Georgi . |
| 3,890,968 | 6/1975 | Pierce et al. . |
| 3,983,480 | 9/1976 | Meserow et al. . |
| 3,990,443 | 11/1976 | Fletcher . |
| 4,001,801 | 1/1977 | Moulet . |
| 4,018,362 | 4/1977 | Ubaud . |
| 4,037,598 | 7/1977 | Georgi . |
| 4,038,981 | 8/1977 | LeFevre et al. . |
| 4,038,982 | 8/1977 | Burke et al. . |
| 4,105,028 | 8/1978 | Sadlier et al. . |
| 4,111,198 | 9/1978 | Marx et al. . |
| 4,137,913 | 2/1979 | Georgi . |
| 4,137,915 | 2/1979 | Kamen . |
| 4,137,940 | 2/1979 | Faisandier . |
| 4,181,130 | 1/1980 | Bailey . |
| 4,207,871 | 6/1980 | Jenkins . |

OTHER PUBLICATIONS

"Medical Electronic Products", Dec. 1980, p. 49.

Primary Examiner—S. Clement Swisher
Attorney, Agent, or Firm—Hume, Clement, Brinks, Willian & Olds, Ltd.

[57] ABSTRACT

A calibrating unit for calibrating infusion pumps and the like includes a drop sensor which operates to generate electrical signals in response to the passage of drops through an intravenous set. The calibrating unit operates automatically to count the number of drops sensed by the drop sensor in a measurement interval which can be set to any one of three different durations. At the end of the measurement interval the calibrating unit automatically stops the count. In addition, this calibrating unit includes an optical simulator for driving the drop sensor at a known rate. This optical simulator allows the entire calibrating unit to be checked for accuracy simply and reliably without requiring dripping fluids or the like.

12 Claims, 10 Drawing Figures

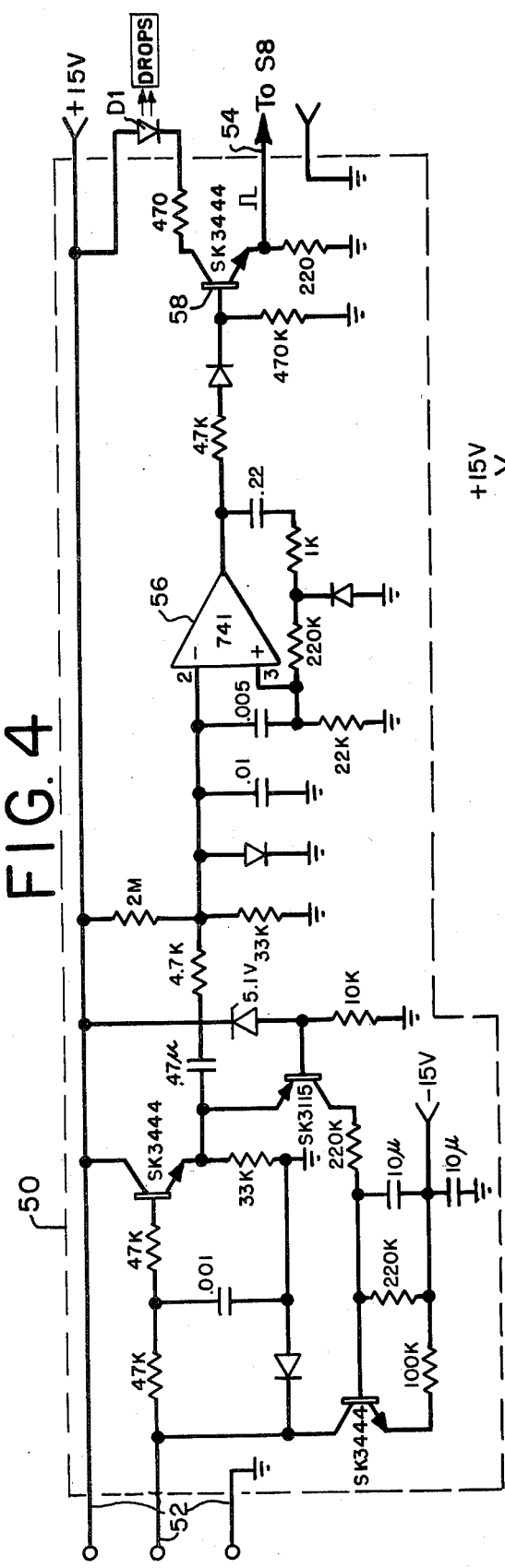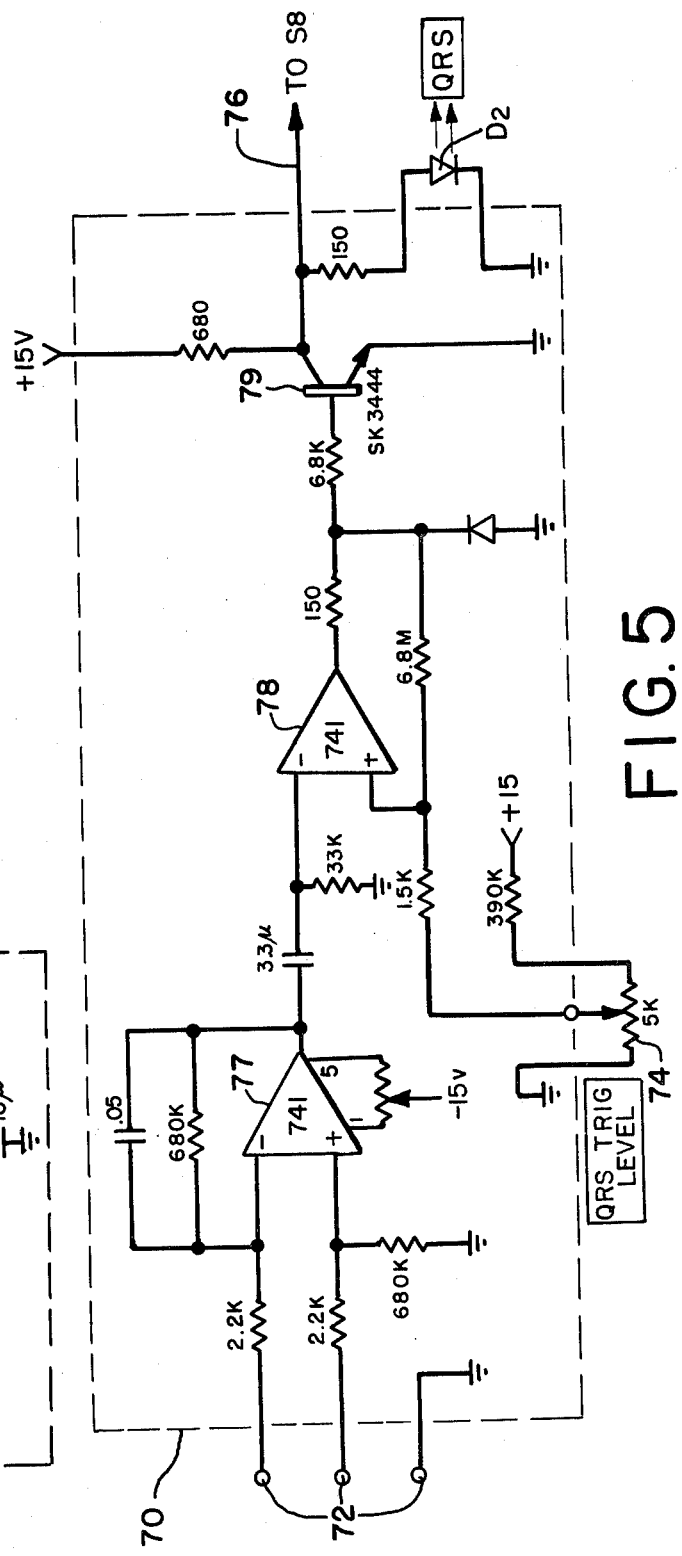
FIG.4
FIG.5

CALIBRATING UNIT

BACKGROUND OF THE INVENTION

This invention relates to an improved calibrating unit for calibrating medical devices such as infusion pumps, which are designed to operate at a periodic, predetermined rate, as well as to a simulator for use with such calibrating units.

Modern hospitals include a wide range of equipment which plays an essential role in modern health care. Calibrating and maintaining this equipment is an important service performed by hospital engineering and technical staffs. For example, a modern hospital will generally make use of a large number of infusion pumps which operate to dispense fluids drop by drop at predetermined rates. Such infusion pumps are routinely used in intravenous administration of medication. Because these infusion pumps operate to control the rate at which medication is dipensed, it is important that they operate reliably and precisely at the desired rate.

In the past, it has been common practice in hospitals to calibrate infusion pumps on a regular basis by means of an individual with a stop watch who manually counts drops dispensed by an infusion pump being calibrated during a manually timed measurement interval. This procedure is intensive in manpower and can result in a considerable burden on the technical staff of a hospital. Similar problems arise in connection with the calibration of EKG simulators.

SUMMARY OF THE INVENTION

The present invention is directed to a calibrating unit which operates automatically and thereby eliminates the need for manual calibration of medical devices such as infusion pumps.

According to a first feature of this invention, sensor means are provided for generating a train of pulses in response to the passage of a series of drops of a fluid. Counter means responsive to the train of pulses act to maintain a count representative of the total number of drops passing the sensor means during a counting interval, such that the counting means automatically stops the count at the end of the counting interval. In addition, means are provided for manually designating a selected one of a plurality of measuring intervals, said plurality of measuring intervals including a first measuring interval which is longer in duration than a second measuring interval. The calibrating unit also includes means for setting the counter interval to correspond to the selected one of the plurality of measuring intervals and means for displaying the count.

According to a second feature of this invention, a calibrating unit is provided with simulator means for generating a simulator signal at a predetermined rate to simulate the passage of a series of drops. The sensor means is responsive to the simulator signal such that the simulating means is operative to drive the sensor means and therefore the counting means at a known rate in the absence of an actual series of drops of a fluid.

The calibrating unit of this invention provides a number of significant advantages. First, since it operates to count drops for a predetermined counting interval, and then automatically to stop and display the count, this calibrating unit operates independently and thereby significantly reduces the time of technical personnel required to calibrate an infusion pump. In addition, since multiple measurement intervals of differing durations are provided, this calibrating unit can be used with short measurement intervals for rough calibration and then with longer measurement intervals for more precise calibration. In this way the calibration time can be kept short if only rough calibration is needed. Also, relatively short calibration periods can be used to adjust an infusion pump approximately and then longer calibrating periods can be used to provide precise measurements of the accuracy of the infusion pump being calibrated.

The simulator of this invention provides the important advantage that the entire calibrating unit can be checked without setting up dripping fluids and the like. In the preferred embodiment described below, the simulator comprises a flashing lamp which is used to drive the same drop sensor used in actual calibration of infusion pumps. Thus the entire calibrating unit, including the drop sensor and all essential circuitry, is exercised by the simulator. In this way the calibrating unit can be routinely checked for accuracy in a simple, reliable manner, without setting up dripping fluids or the like.

The invention itself, together with further objects and attendant advantages, will best be understood by reference to the following detailed description taken in connection with the accompanying drawings.

BRIEF DESCRIPTION OF THE DRAWINGS

FIG. 4 is a schematic diagram of the drop sensor amplifier of FIG. 2.

FIG. 5 is a schematic diagram of the EKG amplifier of FIG. 2.

DETAILED DESCRIPTION OF THE PREFERRED EMBODIMENT

Figure 1:
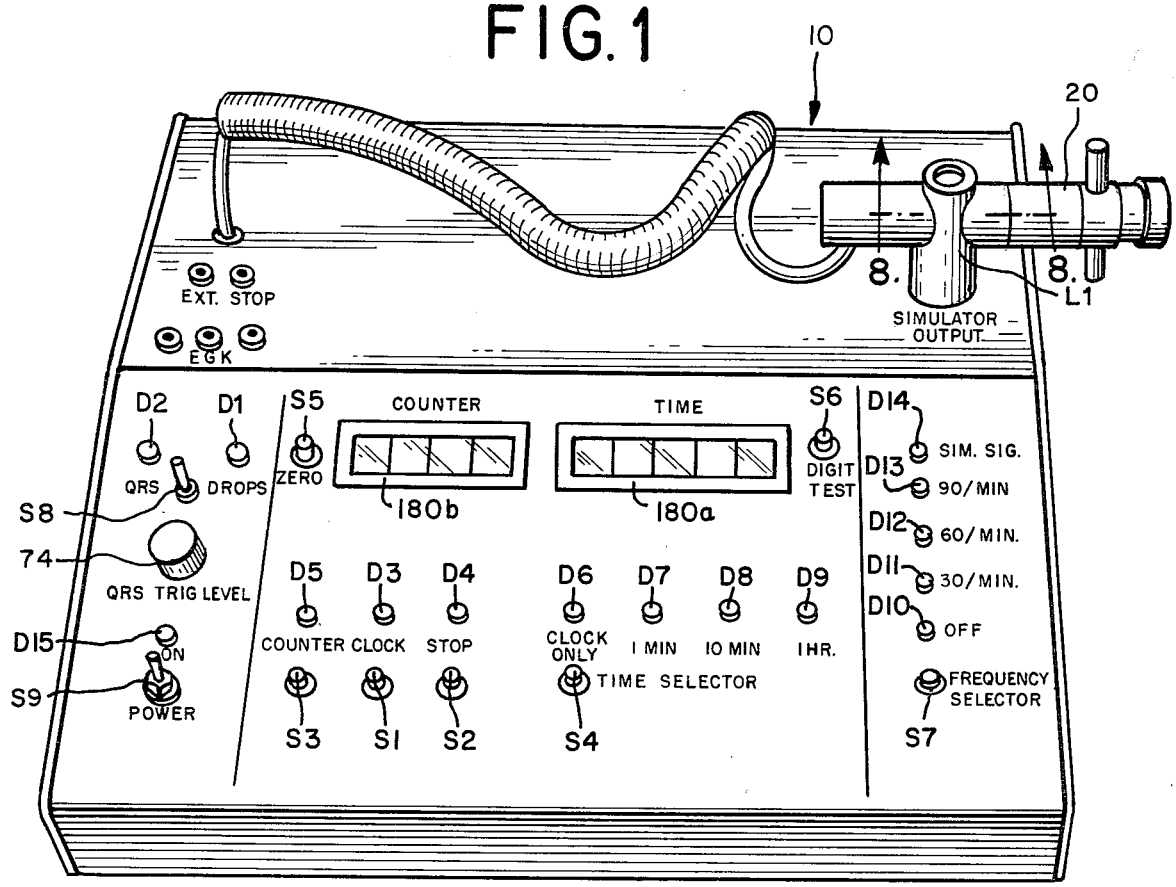
FIG. 1 is a perspective view of a calibrating unit which incorporates a preferred embodiment of the preferred invention.

Turning now to the drawings, FIG. 1 shows a perspective view of the presently preferred embodiment of the calibrating unit of this invention.

As shown generally in FIG. 1, this calibrating unit 10 includes a control and display panel having several distinct sections. In the arrangement shown in FIG. 1, the extreme lefthand portion of the front panel is devoted to input signals which are applied to the calibrating unit 10 and controls related to the initial processing of these input signals. The central section of the control panel contains control switches used to select the desired mode of operation of the calibrating unit 10, along with associated displays. The extreme righthand portion of the control panel relates to the optical simulator included in this calibrating unit 10. The detailed structure and operation of the calibrating unit 10 will be described below in connection with the block diagram of FIG. 2 and the detailed circuit diagrams of FIGS. 3-7.

Figure 2:
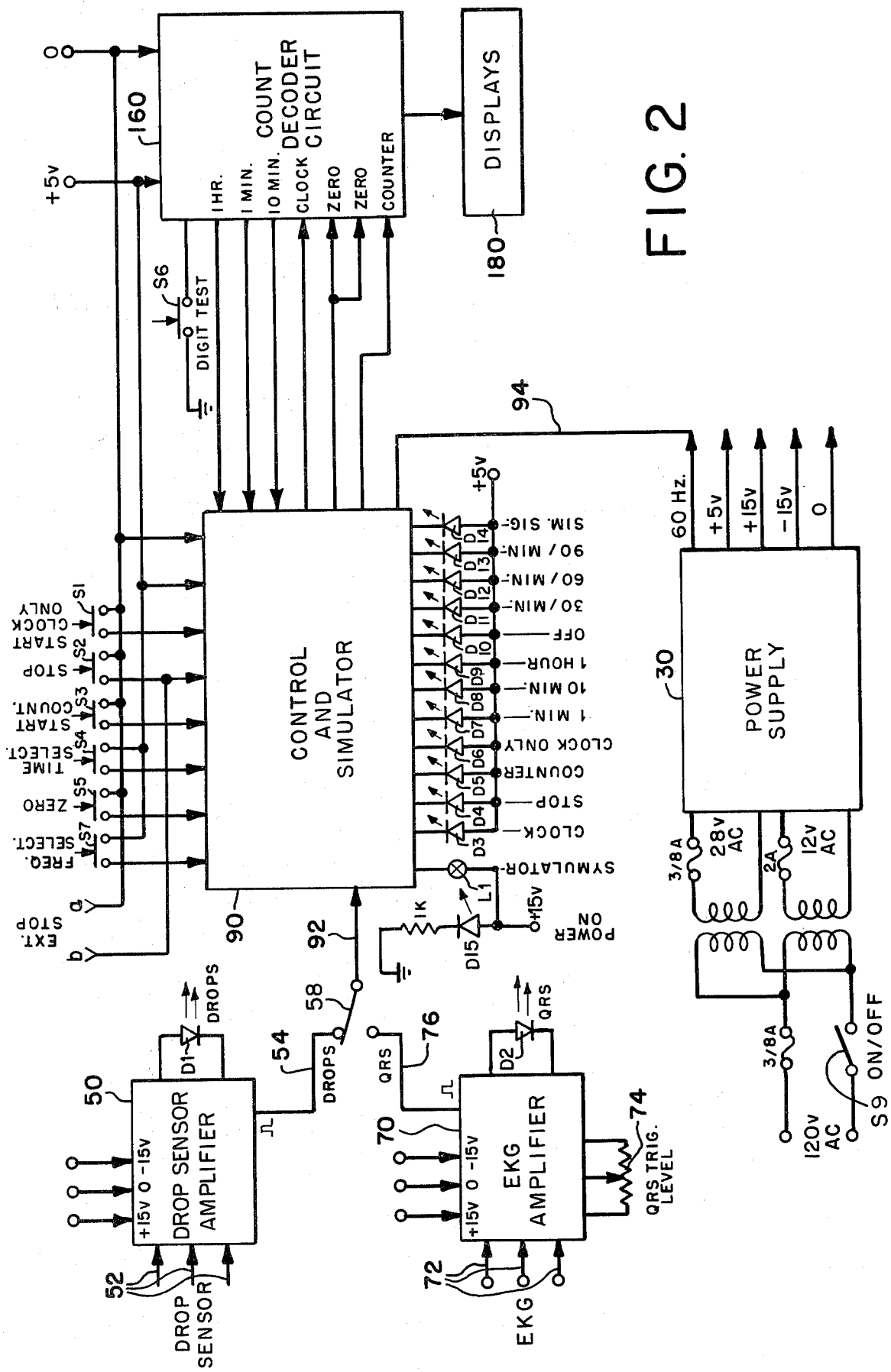
FIG. 2 is a block diagram of the internal circuitry of the calibrating unit of FIG. 1.

As shown in FIG. 2, the calibrating unit 10 incorporates a number of subcircuits, namely a power supply 30, a drop sensor amplifier 50, an EKG amplifier 70, a control and simulator circuit 90, a count decoder circuit 160, and a display circuit 180. Each of these major subcircuits of the circuit of FIG. 2 will be taken up in turn in the following description.

Figure 3:
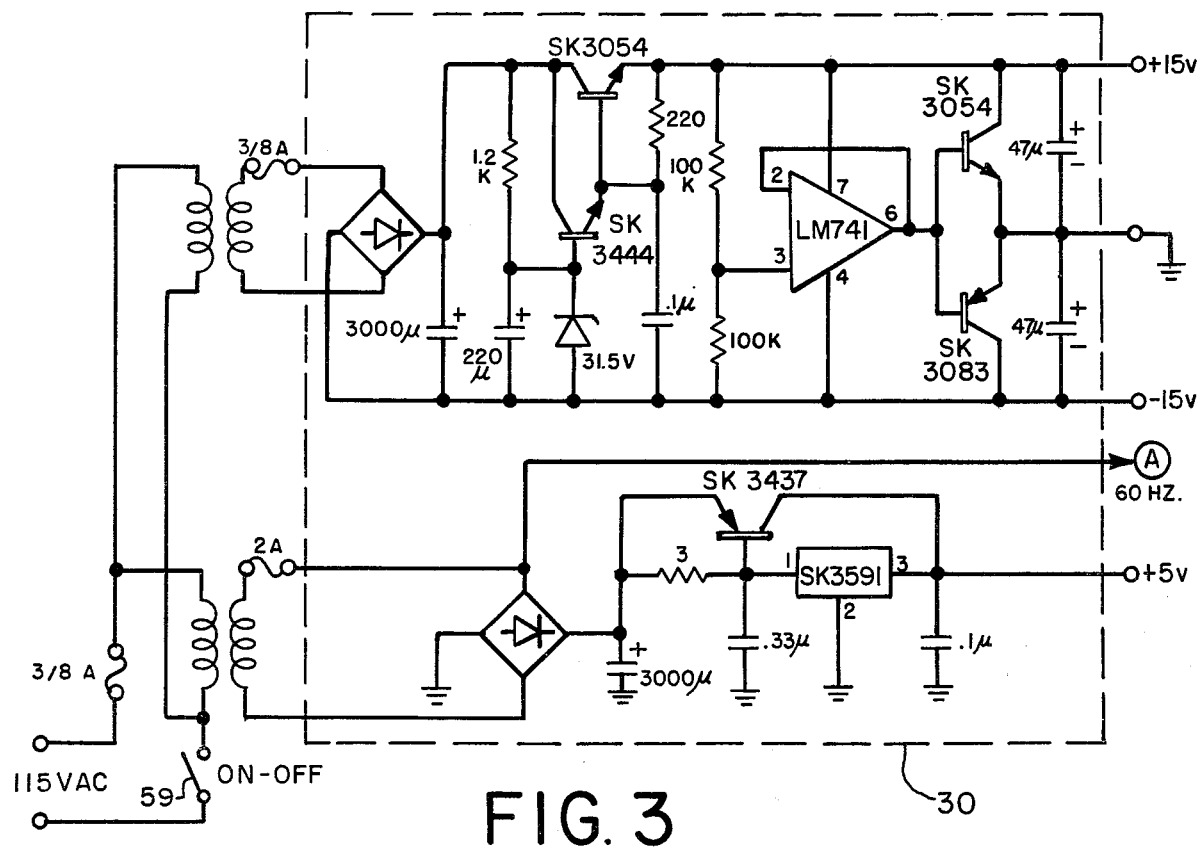
FIG. 3 is a schematic diagram of the power supply of FIG. 2.

FIG. 3 shows a schematic diagram of the power supply circuit 30. This power supply circuit 30 includes means for generating regulated voltages at +15 volts, −15 volts, +5 volts, and ground. In addition, the power supply circuit 30 generates a 60 Hz signal at circuit point A of FIG. 3. As will be explained in detail below, this 60 Hz signal is used for timekeeping purposes in the control and simulator circuit 90. Power switch S9 operates to remove power from the entire power supply circuit 30 and thereby from the entire calibrating unit 10. The circuit of FIG. 3 shows the presently preferred embodiment for the power supply circuit 30. However, it should be understood that the present invention is not directed to improvements in power supplies, and is therefore not limited to the particular circuit shown in FIG. 3. To the contrary, any suitable means for providing desired voltages to power the remainder of the circuit can be substituted for the power supply circuit 30.

FIG. 4 shows a schematic diagram of the drop sensor amplifier 50. This amplifier 50 receives input signals on input conductors 52 from the drop sensor 20 and processes and amplifies these signals to generate output pulses on an output conductor 54. In operation, changed conductivity of a photosensitive element in the drop sensor 20 generates a negative impulse on the inverting input of the operational amplifier 56, which is operating in the monostable multivibrator mode. The resulting output of the amplifier 56 is a positive pulse having a width of about 140 milliseconds. This pulse is used to turn on the transistor 58, thereby raising the emitter voltage of the transistor 58 to about 4 volts and generating a train of pulses which are applied via the conductor 54 to switch S8. Simultaneously, a light emitting diode D1 is pulsed in synchrony with the pulse train on the conductor 54.

The drop sensor amplifier 50 is well adapted for use with commercially available drop sensors manufactured and distributed by Ivac Corporation of La Jolla, Calif. One suitable drop sensor 20 for use with this calibrating unit 10 is that shown and described in U.S. Pat. No. 3,596,515, which issued Aug. 3, 1971 on an application by Richard A. Cramer. This patent is hereby incorporated by reference herein for its description of a suitable drop sensor. In general terms, the drop sensor amplifier 50 serves to process the output signal of the drop sensor 20 on lines 52 and to convert this signal into a form suitable for further processing in the control and simulator circuit 90. Of course, it should be understood that in some applications it may be preferable to alter the drop sensor amplifier 50, particularly if other types of drop sensors are used in connection with the calibrating unit of this invention.

FIG. 4 shows a detailed electrical schematic of the EKG amplifier 70. This amplifier 70 serves to process input signals applied via the input conductors 72 in order to generate a train of pulses on an output conductor 76 having a repetition rate equal to the repetition rate of the input signals. This amplifier circuit 70 includes a differential amplifier 77 which generates an output signal as a function of the difference of the signals on its two input terminals. This output signal is in turn applied to a comparator network comprising an amplifier 78. This amplifier 78 compares the output of the differential amplifier 77 with a reference potential defined in part by an adjustable potentiometer 74. The output of the amplifier 78 drives a transistor 79 so as to generate TTL compatable pulses on conductor 76 as well as to drive a light emitting diode D2 in synchrony with the pulses on line 76. As shown in FIG. 2, conductor 76 is connected to switch S8.

In use, the potentiometer 74 is adjusted such that the EKG amplifier 70 senses the peak of the QRS complex of the EKG signal and generates TTL compatable signal pulses on conductor 76 having a repetition rate equal to that of the peak of the QRS complex. It should be understood that the present invention is not directed to specifics of the EKG amplifier 70, and that a wide range of alternate embodiments may be utilized to perform the necessary signal processing functions in order to generate the desired pulses on the conductor 76.

Figure 6A:
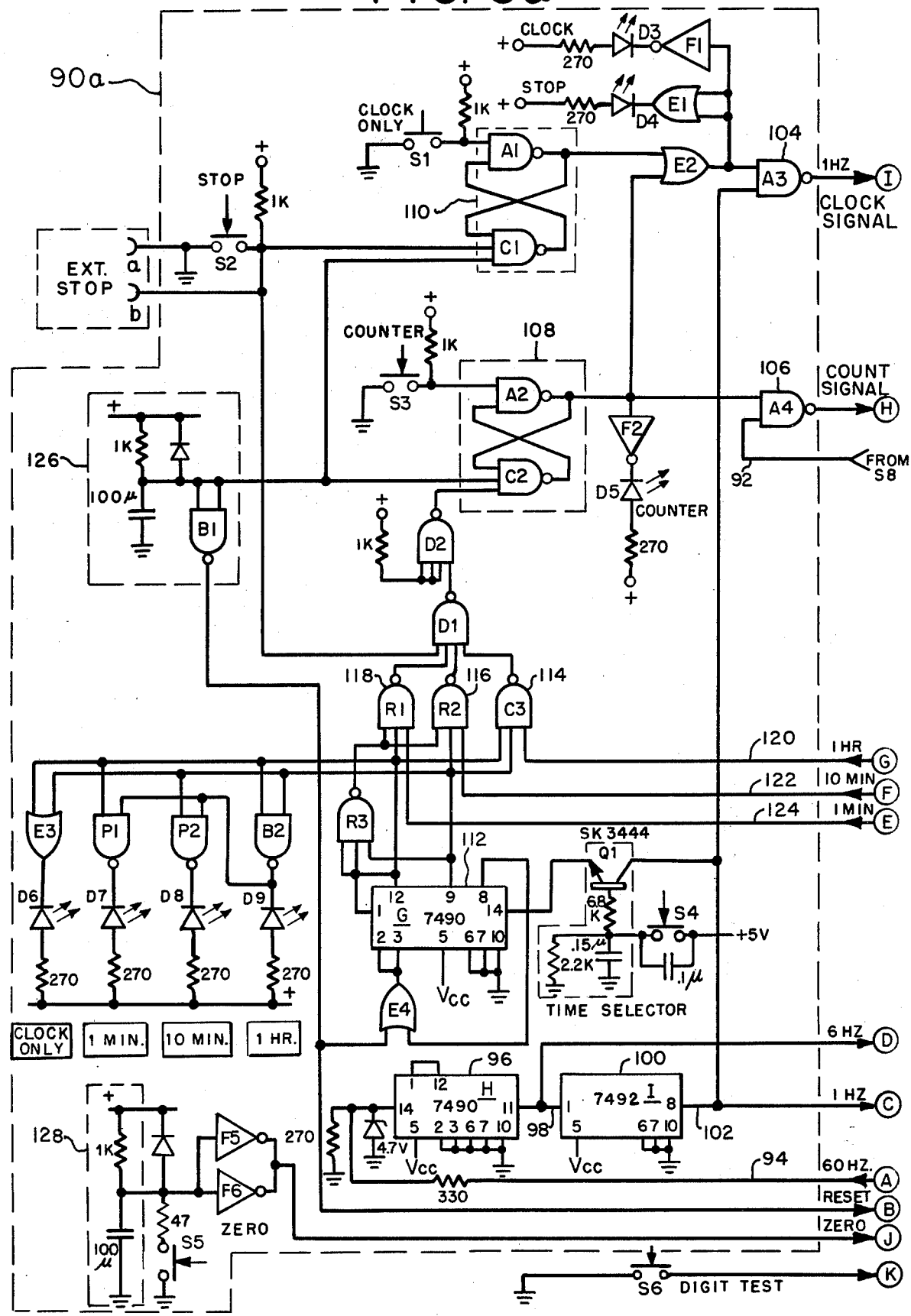
FIG. 6a is a schematic diagram of the control circuit of FIG. 2.
Figure 6B:
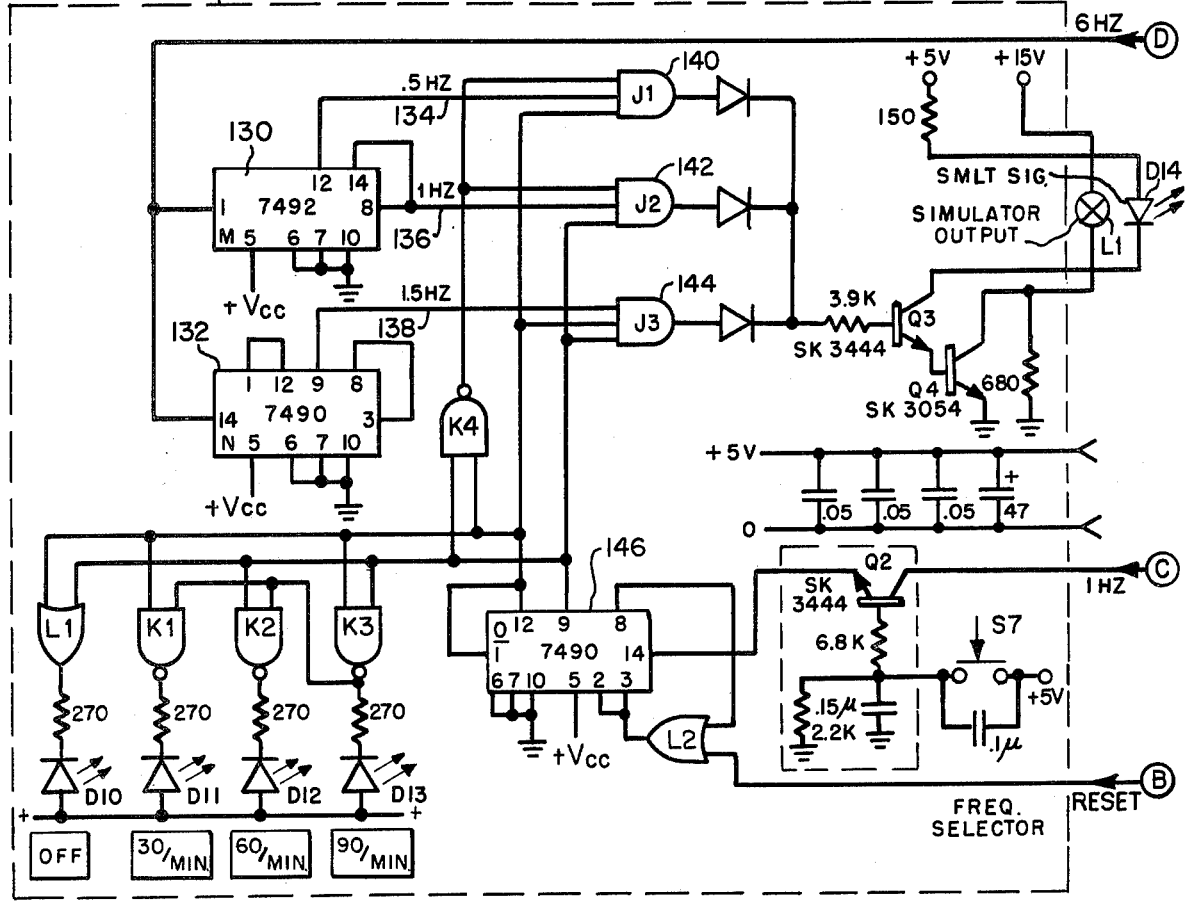
FIG. 6b is a schematic diagram of the simulator circuit of FIG. 2.

Turning now to FIGS. 6a and 6b, the control and simulator circuit 90 comprises a control circuit 90a shown in FIG. 6a and a simulator circuit 90b shown in FIG. 6b. The control circuit 9a of FIG. 6a receives a number of input signals from other parts of the calibrating unit 10. At circuit point A of FIG. 6a the 60 Hz signal from the power supply circuit 30 is applied to the control circuit 90a. This 60 Hz signal is divided by ten in the integrated circuit 96 to produce a 6 Hz signal on line 98. This 6 Hz signal is applied as an input to an integrated circuit 100 which operates to divide the frequency of the input signal on line 98 by six, thereby producing a 1 Hz signal on line 102. This 1 Hz signal is gated by a gate 104 and is then applied as a clock signal to a clock 162 included in the counter decoder circuit 160.

In addition, the control circuit 90a includes a gate 106 having a first input connected to a count input line 92 from the switch S8 and a second input which receives a gating signal. The output of this gate 106 is a count signal which is applied to a counter 164 included in the counter decoder circuit 160.

Much of the remainder of the circuitry of FIG. 6a is devoted to controlling the gates 104,106 and indicating the status of these gates. Switch S3 controls a flip-flop circuit 108 to enable both the gate 106 and the gate 104. Thus, a momentary closure of the switch S3 causes a train of 1 Hz clock signals and a train of count signals to be provided to the counter decoder circuit 160. Whenever the gate 106 is enabled, the light emitting diode D5 is activated to indicate that the counter 164 is enabled, and the light emitting diode D3 is activated to indicate that the clock 162 is also enabled.

Similarly, the switch S1 controls the flip-flop circuit 110 to enable the gate 104, thereby providing 1 Hz clock signals to the counter decoder circuit 160. The light emitting diodes D3 and D4 are provided to indicate whether or not clock signals are being provided to the counter decoder circuit 160. The switch S2 operates to control the flip-flop circuits 108,110 to disable the gates 104,106 in response to a momentary closure of the switch S2. Similarly, a shorted connection between the two external stop inputs serves the same function. Thus, the switch S3 can be used to start both the count and the clock signals, the switch S1 can be used to start the clock only, and the switch S2 can be used to stop both the count and the clock simultaneously.

In addition, FIG. 6a includes means for automatically stopping both the clock 162 and the counter 164 after predetermined counting intervals. This means includes a two bit binary counter comprising an integrated circuit 112. The integrated circuit 112 receives an input on pin 14 which is a 1 Hz signal from line 102 gated by switch S4 via transistor Q1. The integrated circuit 112 operates to provide a two bit binary count on output pins 9,12. When the signals on both pins 9,12 are in the logic low state, the light emitting diode D6 is activated and each of the three gates 114,116,118 is disabled. When both output pins 9,12 are in the logic high state, the light emitting diode D9 is activated and gate 114 only is enabled. Similarly, when only the signal on pin 9 is high, the light emitting diode D8 is activated and only the gate 116 is enabled; and when only the signal on pin 9 is low, the light emitting diode D7 is activated and only gate 118 is enabled.

In addition, the gate 114 has an input coupled to a line 120 which carries a signal which goes from the logic low state to the logic high state after the counter 162 has been counting for one hour. Similarly, the gate 116 has an input coupled to a line 122 which carries a signal which goes from the logic low state to the logic high state after the counter 162 has been counting for a period of ten minutes, and the gate 118 has an input coupled to the line 124 which carries a signal which goes from the logic low state to the logic high state after the counter 162 has been counting for a period of one minute.

The output signals of the gates 114,116,118 are used to control the flip-flop circuit 108 in order to stop both the clock 162 and the counter 164 when the line 120,122,124 corresponding to the gate 114,116,118 which is enabled goes to the logic high state. Thus, by using the switch S4 to configure the control circuit 90a such that the selected one of the four light emitting diodes D6-D9 is activated, the control circuit 90a can be configured to stop both the clock 162 and the counter 164 automatically after an elapsed counting interval of either one minute, ten minutes, or one hour. In addition, the control circuit 90a can be configured such that neither the clock 162 nor the counter 164 is disabled after a predetermined counting interval. In this case, the clock 162 and counter 164 run until stopped, either by momentary activation of the stop switch S2 or by a momentary short between the two external stop terminals.

Also included in the control circuit 90a is a reset circuit 126. This reset circuit 126 serves to generate a reset signal immediately after power is applied to the control circuit 90a in order to reset the flip-flop circuits 108 and 110 so as to activate light emitting diode D4 and to reset the integrated circuit 112 so as to activate light emitting diode D6. In addition, this reset signal is transmitted to the simulator circuit 90b as well.

The control circuit 90a also includes a switch S5 which is used to generate a zero signal to zero the displays 160a, 160b. In addition, the reset circuit 128 operates to generate a zero pulse immediately after power is applied to the control circuit 90a.

Turning now to FIG. 6b, the simulator circuit 90b receives as inputs a 6 Hz signal at circuit point D, a 1 Hz signal at circuit point C, and a reset signal at circuit point B. The 6 Hz signal is supplied as an input to two integrated circuits 130,132. Integrated circuit 130 serves to generate a thirty pulse per minute signal on line 134 and a sixty pulse per minute signal on line 136. Integrated circuit 132 serves to generate a ninety pulse per minute signal on line 138. Lines 134,136,138 are applied as inputs to gates 140,142,144, respectively.

These gates 140,142,144 are controlled by the integrated circuit 146 such that at most one of these gates is enabled at any given time. The circuit 146 operates in a manner analogous to that of the integrated circuit 112 previously described in connection with FIG. 6a. This circuit 146 receives a 1 Hz input which is gated by a switch S7 which operates to control a transistor Q2. Pins 9,12 of integrated circuit 146 provide a two bit binary count. When both output pins 9,12 are in the logic low state, the light emitting diode D10 is activated and all three of the gates 140,142,144 are disabled. When pins 9,12 are both in the logic high state, the light emitting diode D13 is activated and gate 144 only is enabled. When only pin 9 is in the logic high state, the light emitting diode D12 is activated and only gate 142 only is enabled. When only pin 12 is in the logic high state, the light emitting diode D11 is activated and gate 140 only is enabled. Thus, the integrated circuit 146 can be used either to disable all three of the gates 140,142,144, or selectively to enable only one of the three gates 140,142,144. When one of the three gates 140,142,144 is enabled the respective train of pulses at either thirty, sixty or ninety pulses per minute is passed to the network of transistors Q3,Q4 so as to pulse both the light emitting diode D14 and the simulator output lamp L1 at the selected rate. In this preferred embodiment the lamp L1 is a fourteen volt, 0.08 amp incandescent lamp, type #382. Thus, the switch S7 can be used to configure the simulator circuit 90b such that the light emitting diode D14 and the lamp L1 are either (1) pulsed at ninety pulses per minute, (2) pulsed at sixty pulses per minute, (3) pulsed at thirty pulses per minute, or (4) not pulsed at all.

Figure 6C:
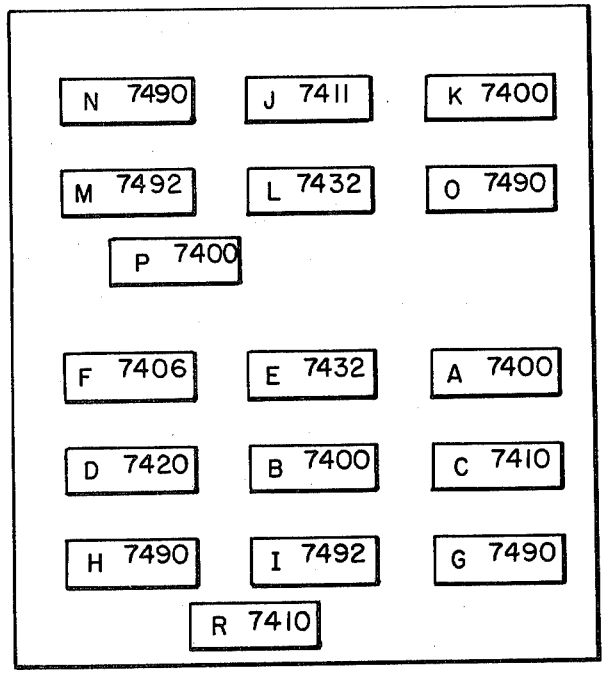
FIG. 6c is a schematic diagram of the layout of integrated circuits on the control and simulator circuit of FIG. 2.

FIG. 6c shows the layout of the integrated circuits used in the control and simulator circuit 90. FIG. 6c identifies the TTL integrated circuit numbers and can be used to provide precise information as to the particular TTL circuits used in this preferred embodiment of the control circuit 90a and the simulator circuit 90b.

Figure 8:
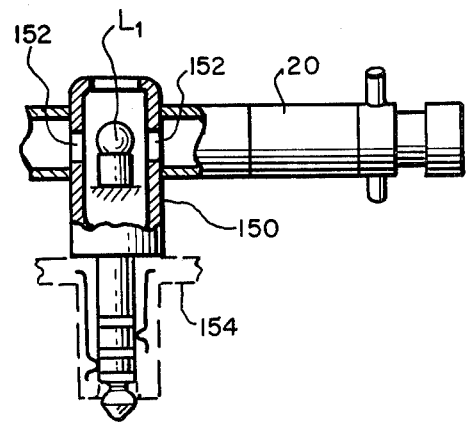
FIG. 8 is a sectional view of the simulator lamp and housing of the calibration unit of FIG. 1, taken along line 8—8 of FIG. 1.

Turning now to FIG. 8, the simulator circuit 90b operates to drive the lamp L1 at a known, predetermined rate. In this preferred embodiment, the lamp L1 is mounted inside a phono jack 150. This phono jack is provided with two opposed openings or light transmissive regions 152 set at the level of the lamp L1. When the phono jack 150 is plugged into a mating receptacle 154 included in the calibrating unit 10, the lamp L1 is flashed as described above to generate an optical simulator signal. In use, the drop sensor 20 is positioned around the jack 150 in much the same way as it would be positioned around the drip chamber of an intravenous set (not shown). The drop sensor 20 is positioned such that the simulator signal generated by the lamp L1 is seen by the photosensor included in the drop sensor 20. The simulator signal generated by the lamp L1 serves to simulate a series of drops of a fluid, thereby causing the drop sensor 20 to generate appropriate signals on the drop sensor amplifier inputs 52.

Figure 7:
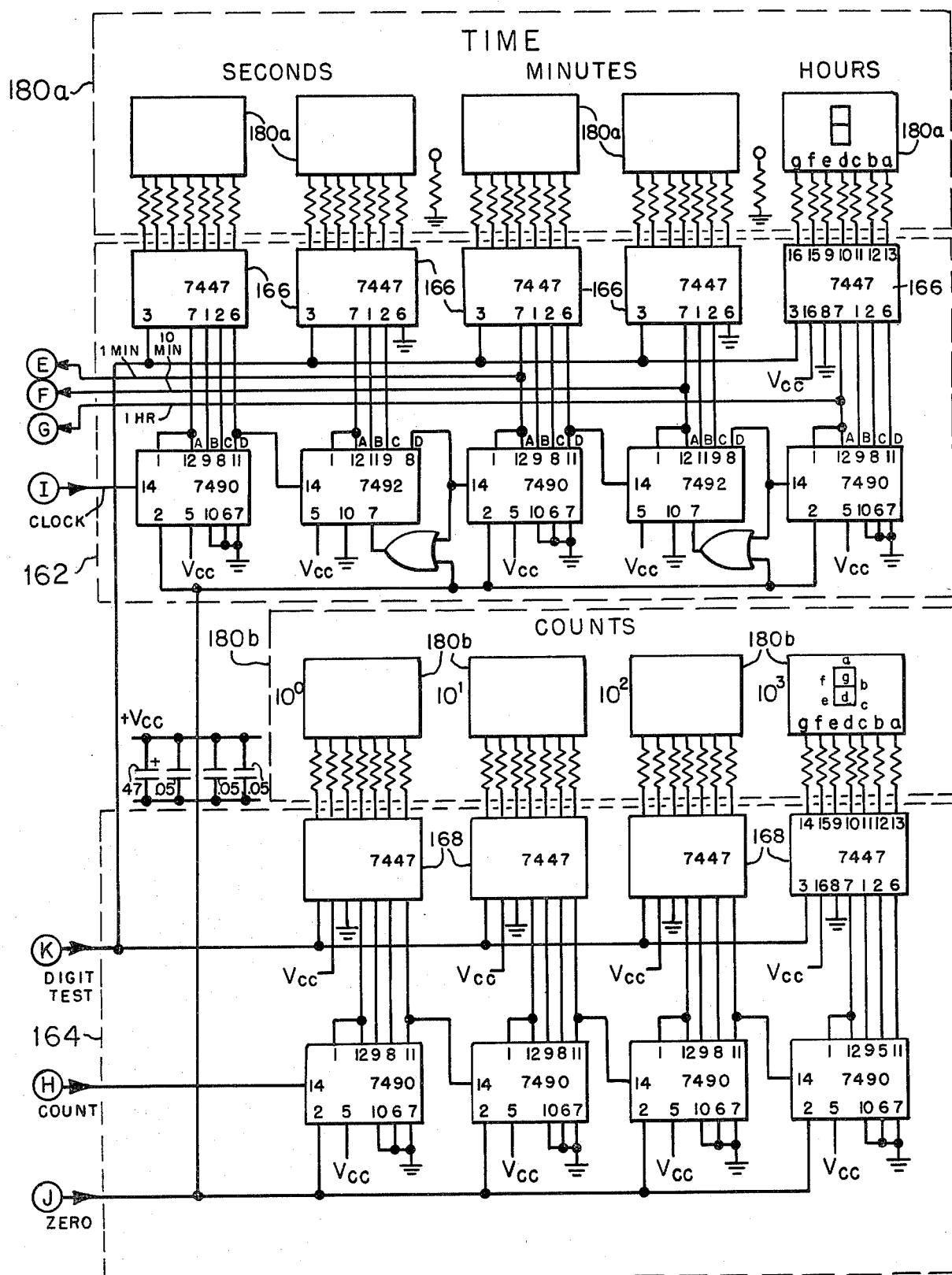
FIG. 7 is a schematic diagram of the count decoder circuit and the displays of FIG. 2.

Turning now to FIG. 7, the counter decoder circuit 160 includes a clock 162 and a counter 164. The clock 162 receives 1 Hz clock pulses from the circuit point I. This clock 162 includes five integrated circuits for counting the clock pulses to determine in hours, minutes and seconds the time the clock 162 has been running. This information is decoded in the decoders 166, and then displayed in the clock display 180a. This clock display 180a is made up of five seven-segment displays such that any time up to nine hours, fifty-nine minutes and fifty-nine seconds can be displayed.

The counter 164, which is made up of four individual integrated circuits and receives count pulses from circuit point H, serves to drive four separate decoders 168. These decoders 168 in turn drive individual seven-segment displays 180b. Thus, the counter 164 can count and display any number of count pulses between 0 and 9999. The counter decoder circuit 160 also includes means for zeroing both the clock 162 and the counter 164 in response to a signal on the zero line, circuit point J of FIG. 7. In addition, a signal at circuit point K of FIG. 7 acts to cause all segments of all displays to be illuminated, thereby providing a display test.

Having explained the structure of the preferred embodiment shown in the drawings, it is now possible to describe the operation of this calibrating unit 10. For example, in order to measure the number of drops dispensed by an infusion pump in ten minutes, the drop sensor 20 is placed around an appropriate portion of the intravenous set (not shown) in order to sense the passage of drops. Then power to the calibrating unit 10 is turned on by means of the switch S9, and switch S8 is positioned to transmit the signal on line 54 from the drop sensor amplifier 50 to the control circuit 90a. The digit test switch S6 is then pressed to ascertain that all displays are functioning properly. Then the time select switch S4 is held down until the light emitting diode D8 is activated, indicating that the control circuit 90a will automatically stop both the clock 162 and the counter 164 after a counting interval of ten minutes. In order to initiate the measurement, the start count switch S3 is activated. Once this is done, the counter 164 will automatically count the number of drops sensed by the drop sensor 20 and the clock 162 will automatically time the period of the counting or measurement interval. When the clock reaches ten minutes the control circuit 90a will automatically stop both the clock 162 and the counter 164. At that point the clock display 180a will register ten minutes and the count display 180b will register the total number of drops sensed by the drop sensor 20 during the ten minutes counting interval. An additional measurement can readily be made merely by zeroing the clock 162 and the counter 164 by means of the zero switch S5, then using the time select switch S4 to set the control circuit 90a to the desired mode of operation, and then pressing the start count switch S3 to begin the measurement.

The calibrating unit 10 can also be used to time the interval required to dispense a predetermined volume of liquid. In order to do this, the time select switch S4 is used to place the control circuit 90a in the clock only mode, in which the light emitting diode D6 is activated. In this mode, the clock 162 and the counter 164 will run until stopped, either by pressing the stop switch S2 or by shorting the two external stop terminals. For example, the two external stop terminals can be connected to means (not shown) for shorting the external stop terminals when a container of fluid has been emptied. When so configured, the calibrating unit 10 will operate to count the total number of drops and to time the period required to empty the container.

In order to use the simulator included in this calibrating unit 10, it is merely necessary to turn on the power by means of the switch S9 and then to depress the frequency select switch S7 until the desired one of the three light emitting diodes D11,D12,D13 is illuminated. This will cause both the diode D14 and the lamp L1 to be flashed at the selected rate. Then the drop sensor 20 is positioned on the jack 150 such that the drop sensor 20 responds to the optical simulator signal generated by the lamp L1. In this way a known input signal is applied to the drop sensor 20. The calibrating unit 10 can then be used to count the number of "drops" counted by the drop sensor 20 in a predetermined measurement interval. In this way the entire calibrating unit 10, including the drop sensor 20, the drop sensor amplifier 50, the control circuit 90a, the counter decoder circuit 160, as well as the displays 180, can readily be checked, without the need for actually setting up dripping fluids or the like. This feature of the calibrating unit 10 allows the calibrating unit 10 to be checked out completely and simply.

Of course, it should be understood that various changes and modifications to the preferred embodiment described above will be apparent to those skilled in the art. For example, other types of drop sensor amplifiers, EKG amplifiers and power supplies can be used. In addition, the control and simulator functions can be implemented in circuits using components other than TTL logic circuits, as can the counter decoder circuit and the displays. The foregoing description of the presently preferred embodiment has been provided merely to illustrate one form of the invention, and not the limit the scope of this invention. Rather, is intended that the scope of this invention be defined by the following claims, including all equivalents.

I claim:

1. An automatic calibrating unit comprising:
sensor means for generating a train of pulses in response to the passage of a series of drops of a fluid;
counter means, responsive to the train of pulses, for maintaining a count representative of the total number of drops passing the sensor means during a counting interval such that the counting means automatically stops the count at the end of the counting interval;
means for manually designating a selected one of a plurality of measurement intervals, said plurality of measurement intervals including a first predetermined measurement interval which is at least ten times longer in duration than a second predetermined measurement interval;
means for setting the counting interval to correspond to the selected one of the plurality of measurement intervals; and
means for displaying the count;
said automatic calibrating unit operating automatically to count and then to display and hold the number of drops detected by the sensor means during the counting interval.

2. An automatic drop counter comprising:
sensor means for generating a train of pulses in response to the passage of a series of drops of a fluid;
counter means, responsive to the train of pulses, for maintaining a count representative of the number of drops passing the sensor means, said counter means having an activated state, in which the count is incremented in response to the train of pulses, and a deactivated state, in which the count is stopped;

means for activating the counter means;

means for automatically deactivating the counter means after a selected measurement interval, said selected measurement interval freely selectable from a plurality of predetermined measurement intervals of varying durations, said plurality of measurement intervals including at least first and second measurement intervals, wherein the first measurement interval is at least six times longer in duration than the second measurement interval; and means for displaying the count;

said drop counter operating automatically to count and then to display and hold the number of drops detected by the sensor means during the counting interval.

3. The invention of claim 1 or 2 wherein the sensor means is optically responsive.

4. The invention if claim 1 or 2 wherein the plurality of measurement intervals comprises three measurement intervals.

5. The invention of claim 4 wherein the three measurement intervals are substantially equal to one minute, ten minutes and one hour in duration, respectively.

6. The invention of claim 1 or 2 further comprising means for automatically deactivating the counter means in response to a stop count signal.

7. A calibrating unit simulator comprising:

sensor means for generating a train of pulses in response to the passage of a series of drops of a fluid;

counter means, responsive to the train of pulses, for maintaining a count representative of the number of pulses in the pulse train in a counting interval;

means for displaying the count; and simulator means for generating a simulator signal at a predetermined rate to simulate the passage of the series of drops at a selected rate corresponding to the predetermined rate, said sensor means being responsive to the simulator signal such that the simulating means is operative to drive the sensor means and therefore the counting means at the predetermined rate in the absence of an actual series of drops of a fluid.

8. The invention of claim 7 wherein the sensor means is optically responsive and wherein the simulator means comprises a light source and means for pulsing the light source at the predetermined rate.

9. The invention of claim 7 further comprising means for setting the predetermined rate to a selected one of a plurality of values.

10. An optical drop counter simulator comprising:

optically responsive sensor means for generating a train of pulses in response to the passage of a series of drops of a fluid, said sensor means comprising a photosensor placed to detect variations in optical brightness associated with the passage of said series of drops;

counter means, responsive to the train of pulses, for maintaining a count representative of the number of pulses in the pulse train in a counting interval;

clock means for maintaining a clock signal representative of the time the counter means has been maintaining the count;

means for displaying the count and the clock signal; and simulator means for generating a pulsed optical simulator signal at a predetermined rate to simulate the passage of the series of drops at a selected rate corresponding to the predetermined rate, the photosensor of the sensor means being responsive to the pulsed optical simulator signal such that the simulating means is operative to drive the sensor means and therefore the counter means at the predetermined rate in the absence of an actual series of drops of a fluid.

11. The invention of claim 10 further comprising means for setting the predetermined rate to a selected one of a plurality of values.

12. The invention of claim 10 wherein the simulator means comprises:

a shaft sized to fit within the sensor means, said shaft defining a light transmissive region;

a light source mounted in the shaft adjacent the light transmissive region such that light from the light source passes through the light transmissive region and is sensed by the photosensor included in the sensor means; and means for driving the light source in a pulsed manner at the predetermined rate.

* * * * *